(12) United States Patent
Bonino et al.

(10) Patent No.: US 7,551,275 B2
(45) Date of Patent: Jun. 23, 2009

(54) SENSOR CALIBRATION SYSTEM AND METHOD

(75) Inventors: Paul S. Bonino, Ontario, NY (US); Gary W. Skinner, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 185 days.

(21) Appl. No.: 11/824,232

(22) Filed: Jun. 29, 2007

(65) Prior Publication Data

US 2009/0000348 A1 Jan. 1, 2009

(51) Int. Cl.
*G01J 1/10* (2006.01)
(52) U.S. Cl. ................. 356/243.1; 250/252.1
(58) Field of Classification Search .............. 356/243.1; 250/252.1
See application file for complete search history.

(56) References Cited

U.S. PATENT DOCUMENTS

| | | | |
|---|---|---|---|
| 3,999,866 A * | 12/1976 | Mathisen | 356/244 |
| 4,171,913 A | 10/1979 | Wildy et al. | 356/325 |
| 5,267,178 A | 11/1993 | Berner | 364/498 |
| 5,268,737 A | 12/1993 | Fukuma et al. | 356/328 |
| 5,272,518 A | 12/1993 | Vincent | 356/405 |
| 5,691,817 A | 11/1997 | Cargill et al. | 356/405 |
| 5,844,681 A | 12/1998 | Alessi et al. | 356/319 |
| 6,035,152 A | 3/2000 | Craig et al. | 399/49 |
| 6,058,357 A | 5/2000 | Granger | 702/104 |
| 6,351,308 B1 | 2/2002 | Mestha | 356/402 |
| 6,567,188 B1 | 5/2003 | Thompson et al. | 358/461 |
| 6,667,803 B1 | 12/2003 | Flessland et al. | 356/319 |
| 6,972,867 B1 | 12/2005 | Venable et al. | 358/1.9 |
| 7,068,366 B2 | 6/2006 | Burk | 356/300 |
| 7,069,164 B2 | 6/2006 | Viturro et al. | 702/85 |
| 7,076,389 B1 | 7/2006 | Gross et al. | 702/116 |

OTHER PUBLICATIONS

Printed RFID, vol. 1, Issue 2, Mar. 2007 (22 pages).
Calibrate Your Scanner, www.desktoppub.about.com/cs/colorcalibration (2 pages), Dec. 11, 2006.

* cited by examiner

*Primary Examiner*—Roy Punnoose
(74) *Attorney, Agent, or Firm*—Alix, Yale & Ristas, LLP

(57) ABSTRACT

Disclosed herein is reference component for a sensor. The reference component comprises a calibration surface and an integrated circuit. The integrated circuit often contains a digital representation of calibration surface properties. A corresponding sensing system, printing system, method of communicating calibration data, and sensor calibration method also are disclosed.

23 Claims, 3 Drawing Sheets

SENSOR CALIBRATION SYSTEM AND METHOD

BACKGROUND

The embodiments disclosed herein generally relate to optical sensors and more particularly to an optical sensor calibration system and a corresponding method for calibrating optical sensors.

Spectrophotometers are used to make color measurements in printing applications. In order for a particular spectrophotometer unit to produce precise color measurements, the unit is calibrated by calculating a number of reflectivities with respect to known reference reflectance values. Usually, these reference values are provided by measuring a white or nearly white standard reference surface that has known reflectivities at the wavelengths of interest.

Two factors are vital to the accuracy of the spectrophotometer's reflectivity calculations. First, the spectrophotometer's measurement of the reference surface must represent the current state of the instrument. This may vary with component age, temperature shifts, or optical contamination. A spectrophotometer is usually equipped with some internal calibration routine or other method to compensate for these changes in system response. The instrument's manufacturer will generally specify the conditions that warrant this occasional recalibration. The second important factor is accurate knowledge of the actual reflectance of the standard reference surface at the precise wavelengths of interest to the spectrophotometer. These values are stored inside the spectrophotometer prior to use. Ideally, the reference surface would be 100% reflective across the spectrum of interest (the visible light range for color spectrophotometers), thus making the need for device specific knowledge of reference surface properties unnecessary. However, this would be expensive and is not really necessary in practice. Another possible scenario would be to use reference surfaces that have identical reflectance properties from one unit to the next, thus allowing interchangeability, but in general this would not be practical.

The current technique is that manufacturers characterize and serialize each individual reference surface. The vendor provides the buyer with an exact specification of reflectance and color of the reference material. The spectrophotometer and reference surface are shipped as "siblings" and must remain together. Sometimes at the time of manufacture the reflectance data for the reference surface is pre-loaded into non-volatile memory (NVM) on the spectrophotometer. Often, manufacturers publish reflectance data for an individual reference surface in printed form so that it can be manually loaded into the spectrophotometer. This might be necessary due to memory failure in the spectrophotometer, or if the reference surface requires replacement due to loss or damage. However, this practice presents logistical difficulties and introduces the potential for human error. Furthermore, in order to maintain color measurement accuracy over the life of the instrument, a spectrophotometer periodically is recalibrated using the reference surface. Recalibration may be difficult or impossible if the reference surface is lost or damaged.

U.S. Pat. No. 5,267,178 describes a spectrophotometer equipped with a serial interface to which a bar code reader can be connected. Using the bar code reader, calibration and configuration data or functional commands for the spectrophotometer can be read from the bar code and transmitted to the computer in the spectrophotometer. U.S. Pat. No. 5,267,178 also mentions storing the data on another type of data carrier such as one that can be read by a conventional reading device, such as a magnetic tape reader or a diskette drive, instead of a bar code reader.

Various disclosures are available involving the calibration of sensors that are affiliated with printing devices. Commonly assigned U.S. Pat. No. 6,972,867 involves in-line image quality testing of a printer. Commonly assigned U.S. Pat. No. 6,567,188 describes a calibration system for an input scanner for a copier. U.S. Pat. No. 6,035,152, also commonly assigned, describes calibration of a printing machine by measuring test patches on an imaging surface.

It would be useful to develop a method by which relevant parameters would be stored and communicated automatically between a reference component and an optical sensor, thus eliminating the need for human intervention, facilitating hardware interchangeability and eliminating unique dependencies between the reference component and the optical sensor.

SUMMARY

One embodiment is a reference component for a sensor. The reference component comprises a calibration surface and an integrated circuit. Usually, the integrated circuit contains data associated with a particular reference component. In most cases, the integrated circuit contains a digital representation of calibration surface properties. The reference component often is for an optical sensor. The calibration surface properties typically include at least one of reflectance, absorbance and transmittance.

In many cases, the integrated circuit comprises an automated communication interface. The automated communication interface can be configured to electronically transmit a digital representation of calibration surface properties to the sensor. The automated communication interface can comprises hardwired electronics and/or wireless electronics such as RF electronics.

Another embodiment is a sensing system comprising a sensor and an interchangeable reference component for the sensor. The interchangeable reference component comprises a calibration surface and an integrated circuit containing a digital representation of calibration surface properties.

A further embodiment is a printing system comprising a printer, an optical sensor and a reference component for the optical sensor. The reference component comprises a calibration surface and an integrated circuit containing a digital representation of calibration surface properties.

Yet another embodiment is a method of communicating calibration data to a sensor, comprising obtaining a reference component for the sensor, the reference component comprising a calibration surface and an integrated circuit containing a digital representation of calibration surface properties, electronically connecting the reference component with the sensor, and transferring calibration data from the reference component to the sensor.

A further embodiment is a method of calibrating a sensor comprising obtaining a reference component for a sensor, the reference component comprising a calibration surface and an integrated circuit comprising a digital representation of calibration surface properties, querying the reference component for the digital representation of calibration surface properties, measuring a property of the calibration surface using the sensor, and updating a sensor algorithm based on the measured property.

DETAILED DESCRIPTION

Figure 1:
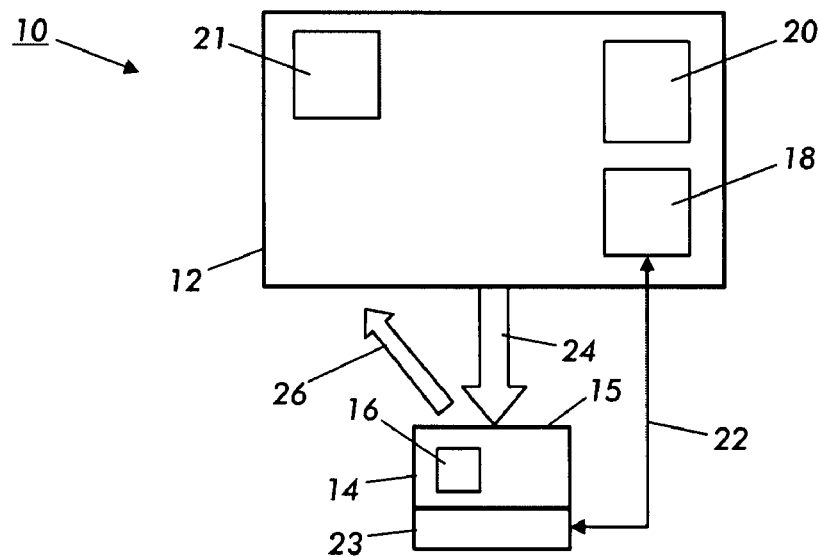
FIG. 1 schematically shows a sensor calibration system according to one embodiment.

The embodiments described herein provide a reference component that includes electronic circuitry containing a digital representation of its unique properties. The circuitry may also include other identifying characteristics of the reference component, thus providing an "electronic signature" for a particular reference component. In some embodiments, a communication interface is incorporated into the electronic circuitry of the reference component in order that the necessary parameters can be electronically transmitted to a sensor that is to be calibrated. The sensor can query the calibration surface for its signature data and use the information for calibration or other purposes. The reference properties and other identifying characteristics can be contained in a tagging device containing electronic circuitry. The system and method are particularly well suited for use with optical sensors, including in-line spectrophotometers associated with digital printers, lithographic printers, and other printing presses.

A "reference component" as used herein is a device that contains a calibration surface for use in calibrating a sensor. As used herein, a "sensor" is an electronic measuring device that is capable of being precisely calibrated. An "optical sensor" is an electronic optical measuring device that is capable of being precisely calibrated. As used herein an "automated communication interface" is an electronic interface that is capable of effecting automatic communication between a reference component and a sensor. An "integrated circuit" as used herein is a microelectronic device that integrates such elements as transistors, resistors, dielectrics and capacitors into an electrical circuit possessing a specific function. A "calibration surface" is a reference surface used for calibration of a sensor. "Calibration surface properties" herein refer to properties that are measured in order to calibrate a sensor.

A "spectrophotometer" as this term is used herein is a color-measuring device that illuminates a color sample of interest with a light source and then measures light reflected and/or absorbed from the sample and interprets the results as a reflectance or absorbance spectrum across a specific range of wavelengths. A "sensor algorithm" as used herein is a formula for converting measured properties into desired units. For the purposes of discussion herein, the term "printer" as used herein shall include all different types of physical printers and output devices, or other hardcopy or document rendering apparatus and devices.

The use of an electronic signature incorporated into the reference component removes the necessity of keeping a specific calibration surface physically matched with a specific spectrophotometer throughout the life of the spectrophotometer by adding certain electronic capability to the calibration surface assembly itself. During manufacture, the calibration surface reflectance spectra can still be measured with a very precise reference spectrophotometer, but instead of mating the specific calibration surface with a specific spectrophotometer and storing the calibration surface reflectance data in the spectrophotometer's nonvolatile memory (NVM), the data can be stored in NVM that physically resides with the calibration surface. This information can be accessed by the spectrophotometer when required for instrument calibration. Very little NVM is actually required for this application, as the data set is small. A typical representation of a visible reflectance spectrum consists of no more than 36 numbers, each of which can be sufficiently represented with a 16 bit data word, for a total of 72 bytes of memory.

Non-limiting examples of types of memory that can be used include a small serial Flash memory device, a one-time-programmable ROM, or a portion of NVM resident in an embedded microcontroller.

In order to share the reflectance information of the calibration surface with a spectrophotometer (or test equipment), in many cases the calibration surface electronics implement a suitable data communication interface. This interface is capable of indicating the presence of the reflectance surface to the host spectrophotometer, accepting requests for reflectance data, and transmitting the signature reflectance parameters of the reference component to the host spectrophotometer. The host spectrophotometer is designed to comprehend this communication interface. Implementations of the physical interface itself might include, but are not limited to hard-wired technologies such as SPI, I²C, CAN, RS232 or USB. Possible implementations might also include wireless technologies, including but not limited to Bluetooth, Zigbee, Wi-Fi, or RFID.

Various techniques can be used to provide the power needed to operate the electronic features of the reference component. The choice of a power supply depends primarily upon the type of wiring that is used. A hardwired USB implementation could provide power through a USB interface. A reference component having a RFID tag would likely utilize RF energy to energize the necessary components. Other suitable power sources include IR, magnetic, solar, battery or a dedicated external power connection.

FIG. 1 schematically shows a sensor system, generally designated as 10. The sensor system 10 includes a sensor 12 and a reference component 14 with a calibration surface 15. The sensor 12 includes a processor 18, a sensor memory 20 and a user interface 21. When used, the sensor 12 emits a radiant flux 24, such as an emission of light, and the specimen being measured (or the calibration surface 15) produces a resulting radiant flux signal 26, that represents reflectance, transmittance or absorbance, which is then measured by the sensor 12. Often, the sensor 12 is a spectrophotometer and the reference component 14 has a reflective white calibration surface formed from a stable, resilient material such as ceramic, enamel, plastic and/or metal.

In addition to the calibration surface 15, the reference component 14 includes a processor 23 and an electronic reference memory 16. Typically the processor and memory are part of integrated circuits mounted on the reference component with a suitable adhesive. The memory 16 contains calibration data. The processor 23 contains software used in transferring the calibration data to the sensor 12. The processor usually also includes a sensor-reference interface that can be configured to electronically connect the sensor 12 to the reference component 14. The saved reflectance spectrum can be uploaded via the sensor-reference interface 22. While the interface typically is incorporated into the reference component 14, it also can be partially or fully incorporated into the sensor 12, or can be located between the sensor 12 and the reference component 14.

Figure 2:
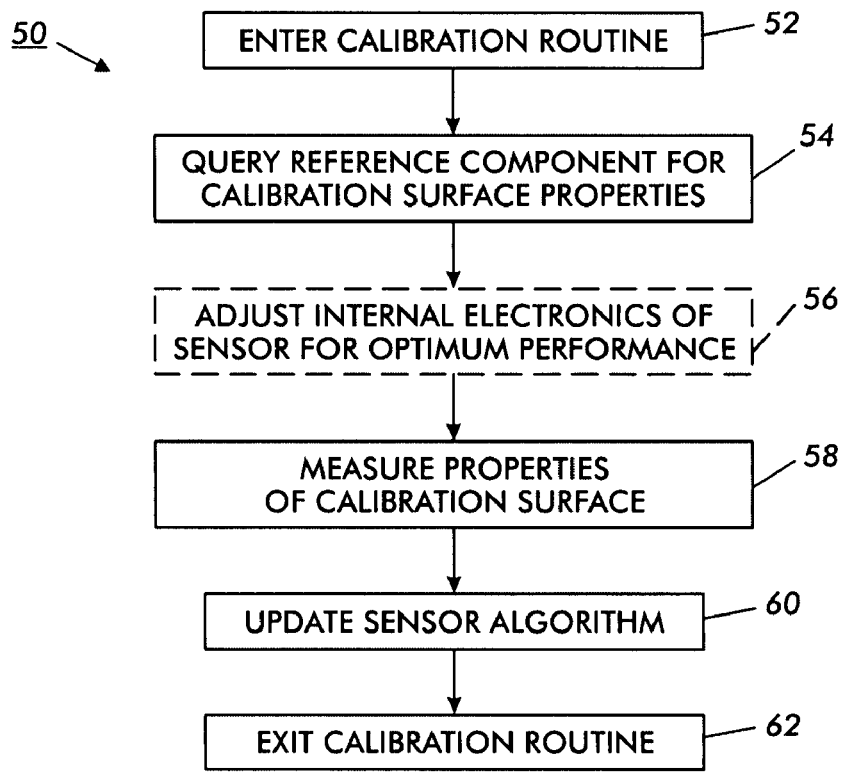
FIG. 2 is a flow chart showing a process of using the sensor calibration system depicted in FIG. 1.

FIG. 2 is a flowsheet depicting a calibration method for a sensor. While the description is directed specifically to an optical sensor, the method can be applied to other types of sensors. When the sensor is to be calibrated, the calibration surface is positioned at or near the location at which specimens are positioned to be read by the sensor. In some cases, the calibration surface is mounted proximate the sensor. The user enters a calibration command at 52 employing the user interface of the spectrophotometer. The reference component is queried at 54 for the digital representation of calibration surface properties. Optionally, the internal electronics of the spectrophotometer are adjusted at 56 for optimum instrument performance. The sensor illuminates the calibration surface using a spectrum of visible light emission. Light reflected off of the calibration surface is measured by the sensor at 58. If necessary, the spectrophotometer updates the algorithm of the spectrometer at 60. The calibration routine ends at 62.

Figure 3:
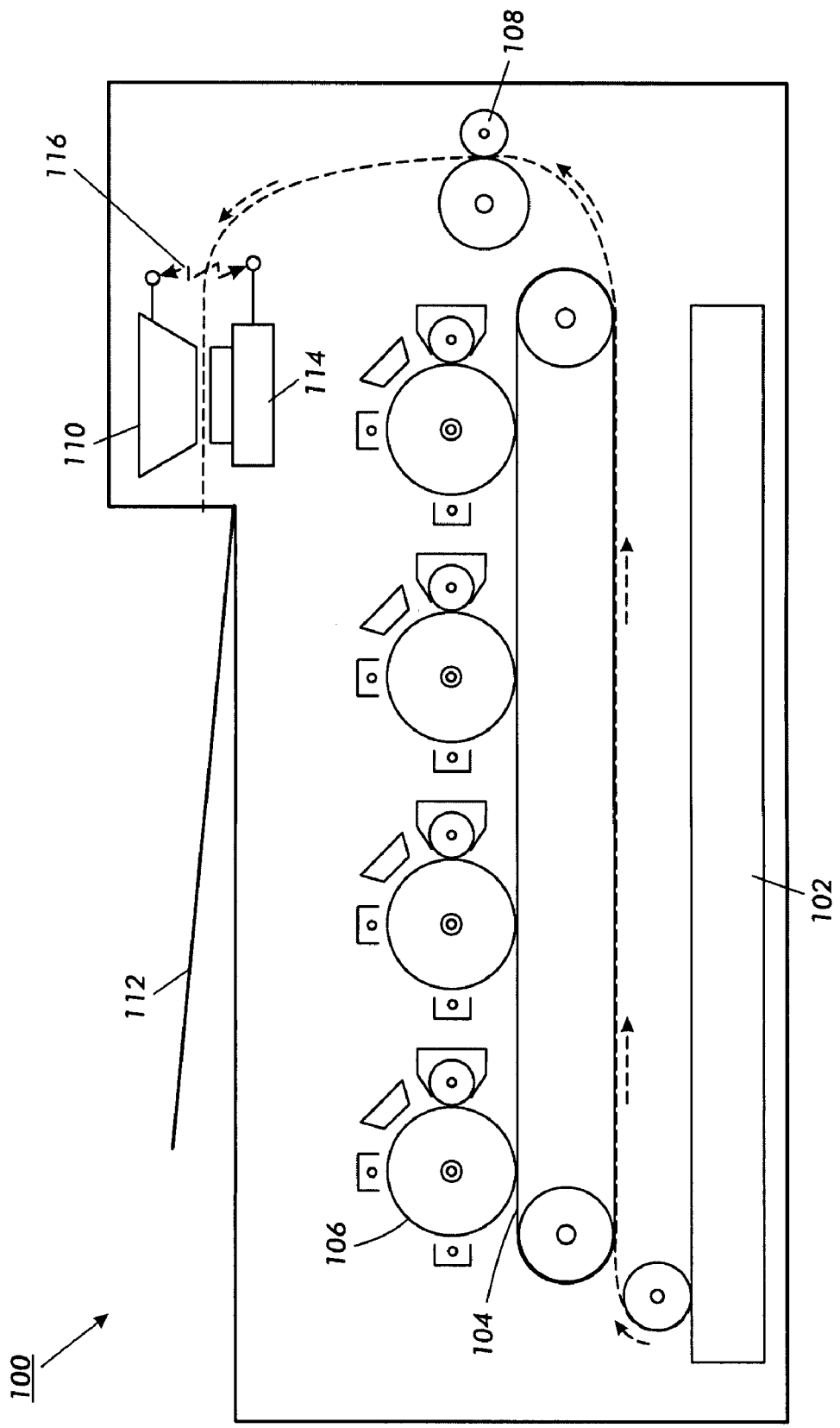
FIG. 3 is a schematic drawing of a printer having a sensor with a reference component that communicates with the sensor using wireless technology.

In FIG. 3, a printer 100 is shown having a reference component that communicates with a sensor using wireless technology. The printer 100 has a paper supply tray 102, a transfer belt 104, a plurality of imagers 106 and a fuser 108. A spectrophotometer 110 is disposed in the printer 100 upstream from an output tray 112. A reference component 114 is mounted adjacent the sensor 110. In response to a query from the spectrophotometer 110 to the reference component 114, a wireless communication interface 116 transmits data, such as a digital representation of calibration surface properties, from the reference component 114 to the spectrophotometer 110.

Figure 4:
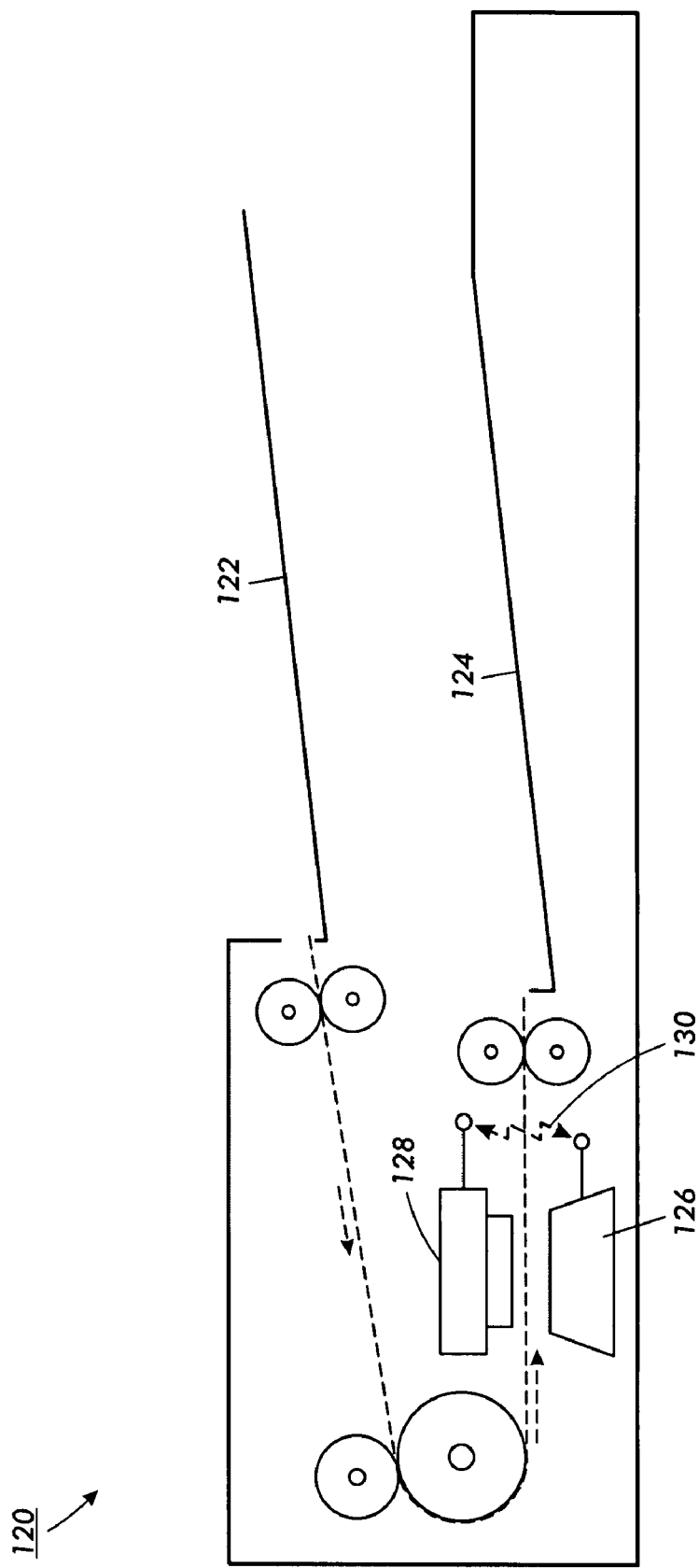
FIG. 4 is a schematic drawing of a scanner having a scanning array with a reference component that communicates with the sensor using wireless technology.

FIG. 4 shows a scanner 120 having a reference component that communicates with a sensor using wireless technology. The scanner includes an input tray 122, an output tray 124 and a scanning array 126. A reference component 128 is mounted adjacent the scanning array 126 to provide a calibration surface for the scanning array 126. In response to a query from the scanning array 126 to the reference component 128, a wireless communication interface 130 transmits data, such as a digital representation of calibration surface properties, from the reference component 128 to the scanning array 126.

In addition to spectrophotometers and scanning arrays, reference components for other types of sensor technologies that require a very precisely mapped calibration surface, including but not limited to calorimeters, densitometers and spectrometers, can be made and used.

It will be appreciated that various of the above-disclosed and other features and functions, or alternative thereof, may be desirably combined into many other different systems or application. Various presently unforeseen or unanticipated alternatives, modifications, variations, or improvements therein may be subsequently made by those skilled in the art which are also intended to be encompassed by the following claims.

What is claimed is:

1. A reference component for a sensor, the reference component comprising a calibration surface and an integrated circuit.

2. The reference component of claim 1, wherein the integrated circuit contains data associated with a particular reference component.

3. The reference component of claim 1, wherein the integrated circuit contains a digital representation of calibration surface properties.

4. The reference component of claim 3, wherein the integrated circuit comprises an automated communication interface.

5. The reference component of claim 4, wherein the automated communication interface is configured to electronically transmit a digital representation of calibration surface properties to the sensor.

6. The reference component of claim 4, wherein the automated communication interface comprises hardwired electronics.

7. The reference component of claim 4, wherein the automated communication interface comprises wireless electronics.

8. The reference component of claim 3, wherein the calibration surface properties include at least one of reflectance, absorbance and transmittance.

9. The reference component of claim 1, wherein the reference component is for an optical sensor.

10. The reference component of claim 1, wherein the calibration surface comprises at least one of enamel, plastic, ceramic and metal.

11. A sensing system comprising a sensor and an interchangeable reference component for the sensor, the interchangeable reference component comprising a calibration surface and an integrated circuit containing a digital representation of calibration surface properties.

12. The sensing system of claim 11, wherein the sensor comprises an optical sensor.

13. The sensing system of claim 11, wherein the integrated circuit comprises an automated communication interface.

14. The sensing system of claim 11, wherein the sensor comprises at least one of a spectrophotometer, densitometer, colorimeter and spectrometer.

15. The sensing system of claim 11, wherein the sensor comprises an inline spectrophotometer for a printer.

16. A printing system comprising a printer, an optical sensor and a reference component for the optical sensor, the reference component comprising a calibration surface and an integrated circuit containing a digital representation of calibration surface properties.

17. The printing system of claim 16, wherein the integrated circuit comprises an automated communications interface.

18. A method of communicating calibration data to a sensor, comprising:
    obtaining a reference component for the sensor, the reference component comprising a calibration surface and an integrated circuit containing a digital representation of calibration surface properties,
    electronically connecting the reference component with the sensor, and
    transferring calibration data from the reference component to the sensor.

19. The method of claim 18, wherein the integrated circuit further contains an automated communications interface.

20. The method of claim 18, wherein the calibration data includes at least one of reflectance, absorbance and transmittance.

21. A method of calibrating a sensor, comprising:
    obtaining a reference component for a sensor, the reference component comprising a calibration surface and an integrated circuit comprising a digital representation of calibration surface properties,
    querying the reference component for the digital representation of calibration surface properties,
    measuring a property of the calibration surface using the sensor, and updating a sensor algorithm based on the measured property.

22. The method of claim 21, wherein the integrated circuit comprises at least a portion of a communication interface between the sensor and the reference component.

23. The method of claim 21, wherein the property of the calibration surface is measured and the sensor algorithm is updated at scheduled intervals.

* * * * *